United States Patent
Robertson

(10) Patent No.: US 11,759,418 B1
(45) Date of Patent: Sep. 19, 2023

(54) COMPOSITION FOR TREATING WOUNDS, DERMATITIS, INFLAMMATION, AND IRRITATION

(71) Applicant: Chrism Products, Inc., Bend, OR (US)

(72) Inventor: Frances M. Robertson, Bend, OR (US)

(73) Assignee: Chrism Products, Inc., Bend, OR (US)

( * ) Notice: Subject to any disclaimer, the term of this patent is extended or adjusted under 35 U.S.C. 154(b) by 0 days.

(21) Appl. No.: 16/725,316

(22) Filed: Dec. 23, 2019

Related U.S. Application Data

(63) Continuation of application No. 15/649,926, filed on Jul. 14, 2017, now abandoned.

(60) Provisional application No. 62/362,754, filed on Jul. 15, 2016.

(51) Int. Cl.
| | |
|---|---|
| *A61K 9/00* | (2006.01) |
| *A61K 9/70* | (2006.01) |
| *A61K 31/04* | (2006.01) |
| *A61K 31/14* | (2006.01) |
| *A61K 31/345* | (2006.01) |
| *A61K 31/4166* | (2006.01) |
| *A61K 47/18* | (2017.01) |
| *A61L 15/44* | (2006.01) |

(52) U.S. Cl.
CPC .......... *A61K 9/0017* (2013.01); *A61K 9/7023* (2013.01); *A61K 31/04* (2013.01); *A61K 31/14* (2013.01); *A61K 31/345* (2013.01); *A61K 31/4166* (2013.01); *A61K 47/186* (2013.01); *A61L 15/44* (2013.01)

(58) Field of Classification Search
None
See application file for complete search history.

(56) References Cited

U.S. PATENT DOCUMENTS

| | | | | |
|---|---|---|---|---|
| 2014/0194482 A1* | 7/2014 | Farber | ........... | A61K 9/107 514/390 |
| 2014/0364495 A1* | 12/2014 | Johnson | ........... | A61P 31/00 514/536 |

OTHER PUBLICATIONS

Neogen Corporation, "Fura-Zone(R) 0.2% Nitrofurazone" Product Information (2013).*
Office Action in corresponding U.S. Appl. No. 15/649,926, dated Jun. 26, 2019.
Kentucky Equine Research Staff, "Pastern Dermatitis in Horses: Causes and Care", https://ker.com/equinews/patern-dermatitis-horses-causes-care, pub. date Jul. 15, 2015.
State Line Tack, https://www.statelinetack.com/item/nitrofurazone-ointment-1-ib/SLT170384 (earliest recorded date Oct. 17, 2013).

* cited by examiner

*Primary Examiner* — Bethany P Barham
*Assistant Examiner* — Barbara S Frazier
(74) *Attorney, Agent, or Firm* — Hovey Williams LLP

(57) ABSTRACT

A composition comprising effective amounts of benzalkonium chloride, allantoin, and nitrofurazone in a water soluble base for treating wounds and skin conditions, such as dermatitis is described. Methods of treating skin conditions and accelerating wound healing are also described.

10 Claims, 17 Drawing Sheets
(17 of 17 Drawing Sheet(s) Filed in Color)

(A)

(B)

(A)

(B)

Left hind pastern    Right hind pastern (A) (B)

Before (C) (D)

After 24hrs

Fig. 19

COMPOSITION FOR TREATING WOUNDS, DERMATITIS, INFLAMMATION, AND IRRITATION

CROSS-REFERENCE TO RELATED APPLICATIONS

The present application is an continuation of U.S. patent application Ser. No. 15/649,926, filed Jul. 14, 2017, which claims the priority benefit of U.S. Provisional Patent Application Ser. No. 62/362,754, filed Jul. 15, 2016, entitled ANTIMICROBIAL AND SKIN CONDITIONING COMPOSITION FOR TREATING MICROBIAL DERMATITIS, INFLAMMATION AND IRRITATION, each of which is incorporated by reference in its entirety herein.

BACKGROUND OF THE INVENTION

Field of the Invention

The present invention relates to compositions for delivering antimicrobials and skin conditioning agents to target tissues, and particularly wound and dermatitis conditions in non-human mammals, and methods for reducing healing time, reduction or elimination of scarring, including in Type Two wounds.

Description of Related Art

The skin is the largest organ of the body providing a protective layer against dehydration, the environment, injury, and infection, as well as regulating temperature and giving the animal its sense of touch. Therefore, the primary goal of a wound management is to achieve healing as quickly as possible. Of secondary, but still high importance, is to effect this healing with as little scar formation as possible.

Depending on the species and age, the skin may be 12 to 24% of an animal's body weight. The skin has 3 major layers: the epidermis or outermost layer which is made of cells called keratinocytes. Keratinocytes provide a protective layer that is constantly being renewed in a process called keratinization. This layer keeps in fluids, electrolytes, and nutrients, while keeping out infectious or noxious agents and serves as a barrier against the inhospitable environment and is the thickest in large animals like horses. Also in the epidermis, melanocytes (located at the base of the epidermis), Langerhans cells (part of the immune system), and Merkel cells (also known as Merkel-Ranvier cells or tactile epithelial cells, are oval-shaped mechanoreceptors essential for light touch sensation). All of the cells described above are found in the epidermis of Equines and are included in this layer. Each of those cells has special functions.

There are two major layers below the epidermis. The dermis or middle layer, and the sub-cutis that consist mostly of connective tissue to cushion the body. The subcutis is the innermost major layer of skin. It contains the subcutaneous fat and muscles. The twitch muscle is the major subcutaneous muscle. The subcutaneous fat provides insulation; a reservoir for fluids, electrolytes, energy, and a shock absorber. Nerves and blood vessels that supply the skin are also found in the subcutis. Any wounds more serious than minor surface abrasions often tear through both of the layers below the epidermis.

The body has looser skin than the lower legs do, which enables wound edges to be pulled together more easily. The tighter skin in the lower legs creates more tension around the outside of a wound, thus resisting the little bit of contractile activity provided by the myofibroblasts in the granulation tissue. Wounds located on the lower legs also experience more motion, particularly in areas over joints such as the knee, hock or fetlock, where there is a lot of movement, and along the cannon bone where tendons run under the skin to extend and flex the foot. Motion tears apart the new granulation tissue and keratinocyte layer, slowing healing and inciting yet more inflammation.

Wounds on the lower legs may heal slower and therefore be susceptible to the formation of proud flesh as that skin in this location is devoid of a muscle called "panniculus carnosus," which exists elsewhere in the body. This is the muscle horses use when they twitch their skin to shake off a fly. In body wounds, the panniculus carnosus is thought to contribute to wound contraction according to researchers. The absence of this muscle on the leg hinders the contractile force of the skin surrounding wounds in this location.

There are also low oxygen levels resulting from the occlusion (blockage) of the blood vessels within the granulation tissue of wounds on the leg. Oxygen is required for the proper function of inflammatory cells, which clear bacteria and debris from wounds. Because wounds on the lower leg are closer to the ground and the various types of footingtall bedding, sand, dirt, and excrement often present around animals. The legs naturally more likely to come into contact with bacteria, dirt, and other environmental contaminants, all of which will trigger more inflammation if not promptly cleared away.

Dermatitis is a general word for any type of inflammation of the skin, which may have a variety of causes, from allergies to insect bites, to fungal, bacterial, parasitic, or viral infection. It is the word usually used to describe any skin condition before a specific diagnosis is reached. Additionally besides the general description of trauma such as wounds, dermatitis is used to diagnose causes of skin inflammation, including external irritants, burns, allergens, and infection (bacterial, viral, parasitic, or fungal), abnormal itching, called pruritus, which occurs in many skin diseases. Equine dermatitis includes a variety of established subcategories.

Sweet Itch is connected with seasonal allergies caused by insect/midge stings. Equine Pastern Dermatitis occurs in equines affecting the lower legs and is also known as scratches, mud fever, mud rash, or greasy heel. Granulomatous Dermatitis in equines is linked to various parasites, fungi, and bacteria, while Vesicular Dermatitis is sometimes called blister disease.

If the problem reaches the deeper layer (the dermis), fluid discharge, pain, and sloughing or shedding of the skin may occur. Secondary bacterial and yeast infections commonly develop as a result of skin inflammation. If the dermatitis does not improve, the early signs of inflammation (such as redness) become obscured by signs of chronic inflammation (thickening of the skin, color changes, scaling, fluid discharge). Often the skin becomes drier and if itching is not already a sign, it will often develop at this stage. When the layers of the animal skin are damaged by injury or inflammation from Dermatitis there are multi-faceted issues that ensue. Excessive inflammation delays healing, and can lead to pressure necrosis, pain, scarring, and bacteria development.

Wounds, are an injury to living tissue caused by a cut, blow, or other impact, typically one in which the skin is cut or broken.

Healing is typically divided into three or four phases. Where a three phase division most often refers to an initial Inflammatory phase, followed by a Fibroblastic/Proliferative phase, and then finishing with a Remodeling/Maturation phase. In a four phase model, a Hemostasis phase is recognized as distinct from the earliest part of the Inflammatory phase.

Briefly, following a four phase model, the Hemostasis phase is characterized by vascular constriction, platelet aggregation, and fibrin formation. Hemostasis begins immediately after wounding and typically lasts only the first several minutes following trauma and results in clot formation and cessation of bleeding. The Inflammation phase involves infiltration of white blood cells to the area and results in the initiation of innate and adaptive immune responses. The Inflammatory phase typically begins within the first minutes to hours following trauma and may last for up to several weeks. The Fibroblastic/Proliferative phase overlaps the Inflammatory phase, initiating hours after trauma and lasting up to weeks. This results in the regrowth of new epithelial tissue, reformation of the Extra Cellular Matrix and angiogenesis. Finally, Remodeling/Maturation occurs as the inflammatory response tapers off and may last even up to years depending on the wound. This final phase involves collagen remodeling and vascular maturation that may result in scarring.

A complication in wound healing occurs when the well-ordered process of healing is delayed, disrupted or incomplete. In these cases, wounds may remain unresolved and become chronic sources of inflammation and infection. That is, healing must progress in the right stages for proper or complete healing to occur. Wounds heal in a manner dependent upon the stage before it. Therefore, a treatment that facilitates the process or allows a stalled process to re-start can be vitally important to the long-term health of the animal. Current treatments often "skip" a stage resulting in slow healing.

Wounds cared for in a manner that maintained moisture and prevented infection and inflammation also correlated well with the absence of scar tissue following healing. Because scarring greatly influences the skin's structure with respect to the orientation of the collagen-rich fibrous network, the biomechanics of scarred tissue is entirely compromised relative to healthy tissue. Excessive inflammation delays healing and can lead to pressure necrosis, pain, scarring, and bacteria development. Significantly, scar tissue exhibits a considerable reduction in biomechanical function and a greatly reduced resistance to failure (i.e. tearing and re-injury). Therefore, reducing the generation of scar tissue during healing will lead to subsequently improved performance of the tissue later in life and a lower probability of repeated injury.

During the early stage of wound healing, the body fills the gap with granulation tissue. As its name implies, this tissue appears very granular (lumpy) because it contains many blood vessels, which bring oxygen and nutrients to the newly forming skin cells. This tissue creates a base layer over which new keratinocytes, produced by the intact skin surrounding the wound, will migrate. Known as "epithelialization," this process enables the keratinocytes to work their way from the edges toward the center of the wound, thereby forming a new epidermal layer. First visible as a pale pink border at the wound's periphery, the new epidermis forms into scar tissue. It is not as strong as the original tissue and is devoid of hair, pigment and various other normal skin components, such as sweat glands.

Meanwhile, cells within the granulation tissue, called "myofibroblasts," pull the wound edges closer together in a process known as "wound contraction." This process complements the epithelialization by decreasing the surface area of the wound that the migrating keratinocytes must cover. In wounds located on the leg of a horse, about 30 percent of healing is accomplished by contraction while 70 percent relies on epithelialization.

Depending on the size and depth of the wound, granulation tissue will take days to weeks to fill the gap until it is level with the surrounding wound edges. In a normally healing wound, the granulation tissue stops growing once it has closed the gap and the keratinocytes start building the new scar tissue over it. Sometimes, however, the granulation tissue continues to grow, mushrooming over the skin surrounding the wound. This is what we call exuberant granulation tissue, or proud flesh. Proud flesh almost exclusively occurs in wounds of the lower leg and is rarely found in wounds on the rest of the body.

The mushroom shape of proud flesh hinders the contractile activity of the myofibroblasts and makes the keratinocytes' job much harder. Instead of traveling across a flat surface, the keratinocytes now must move up and over the edge of this lump of granulation tissue, much the way a rock climber would have to maneuver to get up and over an overhanging ledge. This slows down both wound contraction and epithelialization, sometimes stopping them altogether. Left untreated, the mushroom crown of granulation tissue can continue to grow many inches beyond the horse's normal skin surface. The protruding lump of tissue is susceptible to re-injury, which leads to more irritation and inflammation, thereby prolonging the healing process even further. In most cases, proud flesh will not resolve on its own.

What is needed is a therapy that discourages proud flesh rather than the costly 'other' methods used to regain cell renewal, plasticity, and oxygenation. One of the costly options for treating a Proud flesh wound may require a skin graft to encourage healing. Grafting involves surgical resection of the proud flesh and elimination of inflammation from the wound bed, after which the veterinarian takes small pieces of healthy skin from the horse and implants them into holes created in the healthy granulation tissue of the wound. The skin donor sites are in unobtrusive locations, such as under the mane or trail, so the resulting small scars are hardly noticeable. The procedure is done under sedation with local anesthesia with the horse standing. The method has no guarantee of success, but can increase the cost of treating beyond the ability of many animal owners to pay.

Due to the unique nature of wound repair in horses, existing therapies beneficial to other species may not be suitable. Studies are currently in progress to find: quicker decrease in inflammation, oxygenation to the surrounding damaged tissue, ways to increase plasticity, manner in which the tissue is rejuvenated and greater decrease in scarring.

Veterinarians have expressed the assumption that extreme wounds will bear a scar at the trauma area. Maturation occurs as the inflammatory response tapers off. Complete healing may never occur without intervention. It is reported in veterinarian writings that 'the speed with which the animal's extreme wound will heal depends mostly on the size of the original wound (barring any complications)'. Instead of a couple of weeks for healing with a wound to only the first or second layer of the skin, veterinarians predict a much longer healing time in terms of months with a deeper invasive wound or one that has become slowed or has stopped healing and may have succumbed to Exuberant Granulation Tissue.

Therefore, a treatment that facilitates the process or allows a stalled process to restart can be vitally important to the long term health of the animal. There is current research on hard to heal wounds but there is no prescribed formula achieving the goals for wound resolution in difficult cases.

SUMMARY OF THE INVENTION

The present invention disclosure fulfills the aforementioned need in the art by providing materials and methods for treating acute and chronic skin conditions including, but not limited to wounds, dermatitis, infection, irritation, and inflammation using the composition described herein.

Target tissues include areas of skin or tissue afflicted with a lesion or wound, often exhibiting signs of inflammation, dermatitis, infection, or other dermal or deep tissue injuries. Inflammation is characterized by four classic signs: rubor (redness), color (heat), dolor (pain), and tumor (swelling). It occurs when the body comes into contact with toxins, irritants, pathogens, or cells are otherwise damaged as by physical trauma, burns, chemical exposure, or exposure to radiation. Inflammation is a natural process including a number of processes evolved to limit damage and initiate repair. Instances of acute inflammation refer to degeneration of the process toward healing with rejuvenated skin. However, chronic inflammation is a pathologic condition associated with an unresolved injury that can lead to further damage. As used herein "chronic" means a wound or skin condition that has failed to resolve according to normal healing time periods, and particularly a wound or skin condition that has failed to resolve for at least 3 months. The damage may cause permanent swelling appearing in the area of injury as the skin and blood vessels remodel due to the stretching created with constant inflammation. Pus (Suppuration from Neutrophils) further slows the healing process by breaking down fibrin working to fill the defect. To prevent excessive neutrophils from inhibiting healing, the invention clears pustule areas of the wound which allows fibrin to continue its stage in the healing.

As noted, Dermatitis is any inflammation of dermal (skin) tissue which may present in a number of manners and from a variety of causes. In addition to eliciting the characteristics of inflammation listed above, dermatitis may also manifest as scaling, hair loss, pruritus (itching) or other abnormal conditions. Dermatitis, then, is a descriptive term encompassing any number of these symptoms as the skin reacts to an irritant, rather than a cause itself. Dermatitis, therefore, can be caused by biotic and abiotic agents, including, but not limited to bacterial infections, fungal infections, allergy, foreign bodies, psychological, or by some unknown etiology.

Addressing the above target issues with the invention would be for the purpose of avoiding excessive damage and promoting healthy epithelialization. The invention initiates remodeling to regain healthy connective tissue, circulation, oxygenation, and cell growth.

Infection is the invasion and multiplication of microorganisms in body tissues. Clinically, this involves an organism leaving its reservoir, gaining entry into the body through a portal (in skin infections this is often, but not limited to, cuts or abrasions), evasion of host immune defenses, replication, and damage to cells. Infection of the skin may be self-limiting, may persist over a long period of time resulting in chronic inflammation at one or more sites, or may be progressive and lead to more serious injury to the animal.

Dermal injuries occur when the skin (dermis or epidermis) comes into contact with toxins, irritants, pathogens, or cells are otherwise damaged as by physical trauma, burns, chemical exposure, or radiation exposure; as outlined above.

Injury is defined as an occurrence of cellular damage from any of the aforementioned causes Deep tissue injuries are those injuries to the dermis resulting from the causes listed above, that involve sub-dermal tissues, including, but not limited to fat, muscle, or bone.

Acute conditions typically occur from traumatic injury or the recent onset of an infection, however, they may include small cuts, abrasions, or exposures to toxins which may show subtle symptoms of dermatitis before developing into more severe conditions such as the formation of scabs, blisters, or scaling without intervention. Conditions originating from even relatively small injuries or infections, as well as more extensive trauma can worsen over time. Physical injuries that are left untreated often become infected leading to either severely acute conditions resulting from the combined impact of the trauma and infection or chronic areas of injury that persist indefinitely. This is especially the case with field animals including, but not limited to, horses. This is often the result of these animals not tolerating bandages (if bandaging of the area in question is even possible), lack of constant oversight (e.g. where grazing fields are extensive), or simply repeated exposure to conditions (e.g. tall, wet grasses). Furthermore, these conditions may occur on the feet, legs, or underside of an animal that may be difficult to keep clean even under ideal conditions.

The invention is intended for any of the aforementioned conditions, whether acute or chronic. It is specifically intended for animals including, but not limited to, equines, which are particularly susceptible to these types of conditions.

In horses, the incidence of traumatic wounds is especially common, and these wounds further have a higher incidence of infection when compared to similar wounds in humans or small animals. Of particular interest in equine care are wounds to the extremities, where horses have significantly poorer blood supply and tissue oxygenation than the thorax. These deficiencies may lead to greater colonization by microorganisms, leading to chronic wounds or poor healing and scar formation.

Equine Pastern Dermatitis is a syndrome including inflammation and/or microbial infection of the pastern region of a horse's leg. A variety of factors may lead to the incidence of equine pastern dermatitis, including, but not limited to, wet pasture or boarding environments, cuts and scrapes, ungroomed pastern "feathers", acute or chronic scratching of the area, or exposure to micro-organisms. Animals that are diagnosed with the condition may present with the classic signs of inflammation, tumor (edema or other swelling), rubor (redness), calor (heat), and dolor (pain/sensitivity). However, animals may also present with scarring, persistent wounds, scabs, exudation, matting of the hair/feathers, lameness, pruritus, alopecia, or more advanced signs including fibroblastic proliferation, open fissures, or hyperkeratosis. Many conditions are considered under Pastern Dermatitis, but there are conditions that extend beyond the pastern of the equine.

Draft horses are particularly vulnerable to equine pastern dermatitis because they often have long "feathers" (hair) of the lower leg. The desire of animal owners to display these characteristics of the breed means that they will often maintain the hair growth, despite the pre-disposition for, or even the presence of, infections in this area. One example of such an infectious condition that may persist chronically in equine species is Melandria (aka Malanders or Mallenders) in the foreleg, or Sallenders in the hind leg. These are scruffy eruptions in the bend of the knee of a horse's leg that may present as blisters or pustules with sore, pink areas and may further include yellow scabs or bleeding cracks in the skin. These feathered breeds also develop another form of dermatitis caused by Chorioptic mange mites also called: "feather mites". With the popularity of the "feathered breeds", the concern and need for a way to curb these conditions has risen. However, the mite issue for horses is not limited to feathered breeds. From Miniature horses to huge Draft breeds, and every breed in between are victims of the tiny mite.

Prophylactic measures, such as maintaining clean, dry indoor stalls during wet weather, clipping of pastern hair (feathers), and delaying turnout to pasture until after morning dew has dried, may limit the occurrence of dermatitis, nevertheless, it will occasionally present.

There are different presentations of Equine Pastern Dermatitis: the mild form, manifesting primarily in alopecia and dry skin; the exudative form, characterized by serous or purulent crusting dermatitis and epidermolysis; and finally, the chronic proliferative form characterized by fibroblastic proliferation, nodule formation, and lichenification. This invention addresses the multitude of issues surrounding Equine Pastern Dermatitis (EPD).

1. If the dermatitis is noticed early, improvement can be attained in 2-3 days.
2. Prolonged EPD can develop multi symptoms, including scar/fibroid tissue covering areas of cracked skin. This results in aberrant healing of the derma which includes non-healing of the cracked or damaged derma of the pastern. The invention has removed scar/fibroid tissue that has covered the wounds for many years.
3. The invention develops softening, oxygenation of the surrounding tissue and reduction of the depth of the cracks apparent on the pastern. The invention promotes the healing of the dermis and the underlying lesions so they may continue to fill in appropriately.
4. This invention was applied to a Gypsy horse (a feathered breed of equine) with a severe case of Chorioptic mange mites, a diagnosis within the description of EPD.

Per the Examples, the large round growths that invaded the entire back of the legs from the knee down, were eliminated in the first 24 hours. Application for 2 more days showed oxygenation and vascularity of the surrounding tissue. The feather mite population responsible for the usual spore/grape sized matter appears to have decreased or been removed from the leg. Bright red spots at attachment points show fresh circulation to the area.

The invention develops cell and tissue softening, oxygenation of the surrounding tissue and reduction of the depth of the cracks apparent on the pastern. The invention promotes the healing of the dermis and the underlying lesions so they may continue to fill in appropriately.

This invention embodies a primary wound/infection composition intended for physical contact with the wound/infected surface. This composition is to be applied following initial cleaning or irrigation and debridement (if deemed necessary) and may or may not be covered by a secondary dressing and/or wrap. The initial cleaning or irrigation is preferably conducted with saline water only, and without use of antibacterial cleansers.

Methods of treating skin conditions or wounds on a subject in need thereof are also described. The methods generally comprise applying a therapeutically effective amount of the composition to the site of the skin condition or wound of the subject to yield a treated site. The treated site, may, but does not need to be, covered with a dressing, gauze, and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure (FIG. 1A is a photograph of a degloving injury on the right hip in the region of the biceps and femoris of a foal.

FIG. 19 shows photographs of (A) left and (B) right hind pasterns of a horse infected with Scratches, and the improvement of the condition 24 hours after application of the composition to the (C) left and (D) right pastern area.

DETAILED DESCRIPTION

Figure 1A:
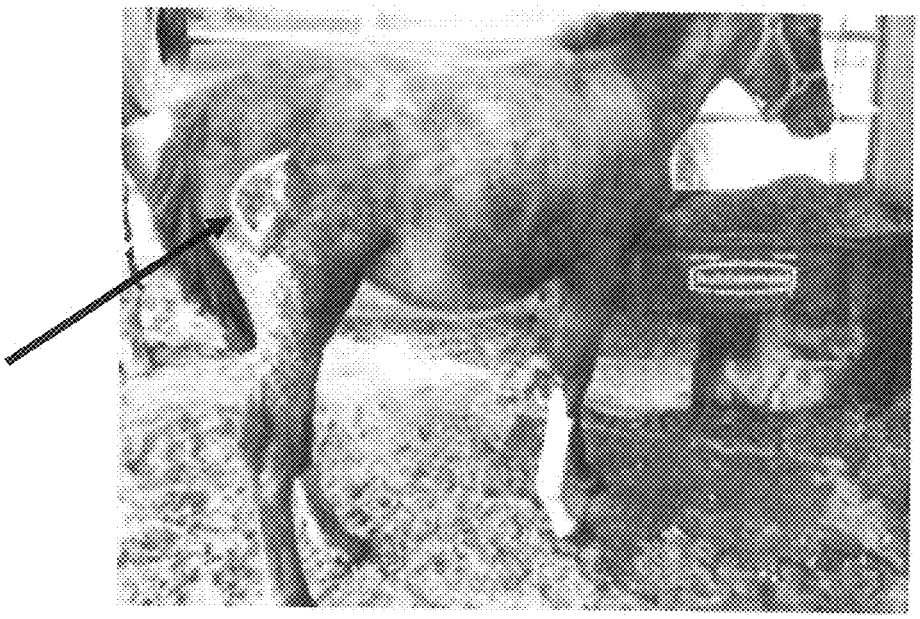
FIG. 1B is a close-up photographic view of the degloving injury.

The present invention is concerned with compositions used to treat acute and chronic skin conditions including, but not limited to wounds, dermatitis, infection, and inflammation. The term "wound" is used herein to refer to injury or disruption to living tissue caused by a lesion, cut, blow, friction, or other impact in which the skin is cut or broken, as well as to incisions into the skin. Thus, the term encompasses incisions, abrasions, cuts, lacerations, burns, avulsions, necrosis, and the like of the skin (epidermis), and can be caused accidentally or purposefully (e.g., such as through surgery). The compositions are useful in "treating" skin conditions and wounds, meaning that the composition can be applied to the site of the wound or skin condition of a subject or administered (topically or injected) to a patient suffering from the wound or skin condition for the purpose of diminishing or eliminating signs, symptoms, or severity of the wound or skin condition.

This invention has found the combination of the ingredients possesses a synergy that creates an unusual and beneficial mixture that surpasses the original uses and results of the individual products have presented in past dermatitis situations. The rapidity and effectiveness of this invention sets it aside from the individual Ingredients. Effectiveness has been shown on chronic conditions over a year old. All techniques and products available to the veterinarian were used in the past, but it was the invention that actually relieved the equines distress and in a matter of days.

In one embodiment of the present disclosure, the disclosure describes a composition comprising (consisting essentially, or even consisting of) effective amounts of benzalkonium chloride, allantoin, and nitrofurazone in a water soluble base. The composition has a gel-like consistency. The inventive compositions maintains a moist environment at the wound or skin condition site whether applied with or without additional dressings or wraps.

In one or more embodiments, the compositions comprise from about 0.10% to about 0.20% wt. nitrofurazone; from about 0.01 to about 0.05% wt. benzalkonium chloride; and from about 0.005% to about 2% wt. allantoin, in a water-soluble base, based upon the total weight of the composition taken as 100% by weight. In one embodiment, the water-soluble base preferably comprises polyethylene glycol and water. One or more coloring agents (dyes) may be added to facilitate visual observation of the application of the composition to the site of the skin condition or wound.

Exemplary components of the water-soluble base include one or more emollients from Cetostearyl Alcohol, Cetomacrogel 1000, liquid paraffin, white soft paraffin, Chlorocrasol, Purified water Q7-9180 Silicone Fluids (0.65 cSt, 1.0 cSt) ST-Cyclomethicone 5-NF Q7-9120 Silicone Fluids (20 cSt to 12,500 cSt) ST-Dimethiconol 40, Dimethiconol Blend 20 Silmogen Carrier, ST-Elastomer 10 Silky Wax 10 ST-Wax 30 Emulsifier 10, Hexamethyldisiloxane (0.65 cSt), Octamethyltrisiloxane (1.0 cSt), Decamethylcyclopentasiloxane, polydimethylsiloxane, Hydroxy-terminated polydimethylsiloxane, hexamethyldisiloxane, Silicone elastomer gel, Stearoxytrimethylsilane, stearyl alcohol, Alkylmethyl siloxane, Alkymethyl siloxane copolyol. Other components include, dextran, glycerin, glucan, gelatin, sodium alginate, and the like can also be used.

Additionally, viscosity can be managed by using a combination of PEG's using a variety of molecular weights. Examples include PURITY pH (Vol. 4) Polyethylene glycol (PEG), identified with the IUPAC Name, 2-hydroxyethyl octadecanoate (PubChem CID: 24762); also known as polyethylene oxide, polyoxyethylene, cremophor A, macrogol-stearate 400, or PEG-stearate (among other names) is a common surfactant that can be used as an excipient for long term stability and to facilitate the absorption of drugs. Other PEG models considered are listed below: 200 4.1-4.8 300 5.4-6.4 400 6.8-8.0 500 8.3-9.6 600 9.9-11.3 700 11.5-13.0 800 12.5-14.5 900 15.0-17.0 1000 16.0-19.0 1100 18.0-22.0 1200 20.0-24.5 1300 22.0-27.0 1400 24.0-30.0 1450 25.0-32.0 1500 26.0-33.0 1600 28.0-36.0 1700 31.0-39.0 1800 33.0-42.0 1900 35.0-45.0 2000 38.0-49.0 2100 40.0-53.0 2200 43.0-56.0 2300 46.0-60.0 2400 49-65 2500 51-70 2600 54-74 2700 57-78 2800 60-83 2900 64-88 3000 67-93 3250 73-105 3350 76-110 3500 87-123 3750 99-140 4000 110-158 4250 123-177 4500 140-200 4750 150-228 5000 170-250 5500 206-315 6000 250-390 6500 295-480 7000 350-590 7500 405-735 8000 470-900.

It is important that the viscosity stabilizes with a specific amount of coalescence, stability and uniformity. Water solubility is preferred for immediate cleansing and reapplication as well as the breathability of a water soluble product versus the potential smothering with oil bases. An important point due to the need for vascularity, oxygenation and circulation to the damaged layer(s) of the skin.

Nitrofurazone, $C_6H_6N_4O_4$, identified with the IUPAC Name, [(E)-(5-nitrofuran-2-yl)methylideneamino]urea (PubChem CID: 5447130); also called nitrofuracin, nitrofural, furacilin, furacin, or furacillin; is a topical anti-infective used against both Gram-negative and Gram-positive bacteria which is also used orally to treat Trypanosomiasis.

Benzalkonium Chloride, identified with the IUPAC Name, benzyl-dimethyl-tridecylazanium (PubChem CID: 2330); also known as Benzalkonium; Alkyl benzyldimethyl ammonium chloride (among other names). It is used in the present compositions as a cationic surfactant to increase drug penetration. It is also beneficial to the other ingredients as an excipient. Benzalkonium Chloride is also beneficial for its local anti-infective properties. It is mixed with the other ingredients with a concentration in the range of 0.01% to about 0.05%, preferably from about 0.1% to about 0.02% by weight. Clinical Studies have found Benzalkonium Chloride to produce mild skin irritation when used at 5% or greater concentration, but not below, concluding that the compound is safe for dermal use at concentrations up to 0.5%.

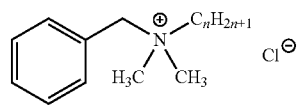

n = 8, 10, 12, 14, 16, or 18

Allantoin is a chemical compound with formula $C_4H_6N_4O_3$. It is also called 5-ureidohydantoin or glyoxyldiureide. It is a diureide of glyoxylic acid. Allantoin is a major metabolic intermediate in most organisms including animals, plants and bacteria. It is produced from uric acid, which is a degradation product of purine nucleobases, by urate oxidase (or uricase).

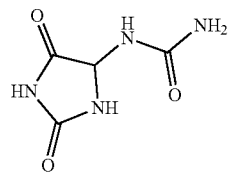 [SMILES: NC(=O)NC1NC(=O)NC1=O]

This invention utilizes Allantoin which is present in botanical extracts of the comfrey plant and in the urine of most mammals. Chemically synthesized bulk allantoin, which is chemically equivalent to natural allantoin, is safe, non-toxic, and compatible with cosmetic raw materials and meets CTFA and JSCI requirements. Several beneficial effects of allantoin include a moisturizing and keratolytic effect, increasing the water content of the extracellular matrix and enhancing the desquamation of upper layers of dead skin cells, increasing the smoothness of the skin; promoting cell proliferation and wound healing; and a soothing, anti-irritant, and skin protectant effect by forming complexes with irritant and sensitizing agents. Scarring inhibits the possibility of further healing and needs to be degraded so that healthy rejuvenated cells can proliferate. Therefore, the nature of the conditions at which this invention is particularly useful are cellular proliferation of tissue areas that have lost vascularity and to excise dead skin cells, thus creating an improved environment for the rejuvenation and the opportunity to increase oxygenation to the wound area.

It has been determined that based on the results from histological analyses, allantoin benefits the wound healing process. By modulating the inflammatory response, Allantoin also promotes fibroblast proliferation and synthesis of the extracellular matrix and acceleration of epithelization of the skin area. This is exactly what the hard to heal, exuberant granulation tissue and, of course, normal healing wounds must have. Allantoin is mixed with the other ingredients of the invention in a solution of about 0.005% to about 2%, preferably from about 0.5% to about 1% by weight.

The following solvents are some of the preferred diluents used to create the solution.

| Solvent | Temp | Concentration |
|---|---|---|
| Water | 20° C. | ca. 0.4% |
| Water | 75° C. | ca. 4.0% |
| Ethanol | 20° C. | ca. 0.1% |
| 5% Glycerin in water | 20° C. | ca 0.8% |
| Propylene glycol | 25° C. | ca. 0.3% |
| 50% Isopropanol in water | 25° C. | ca. 0.3% |

In general, the methods comprise applying or administering a therapeutically effective amount of the composition to the site of the wound or skin condition for a therapeutically effective period of time. In one or more embodiments, the composition is applied as a dressing to the site. The composition and/or dressing may be changed periodically, wherein a fresh amount of composition is applied to the site. Additional physiologically-acceptably non-occlusive dressings, tape, gauze, bandages, combinations thereof, and the like may be used in conjunction with the composition, according to standard wound care protocols, but are not necessary and may be omitted. As used herein, the term "therapeutically effective" refers to the amount and/or time period that elicits the biological or medical response of a tissue, system, animal or human that is being sought by a researcher or clinician, and in particular elicit some desired therapeutic effect(s). For example, in one or more embodiments, therapeutically effective amounts and time periods are those that reduce inflammation and initiate or promote healing of the wound or skin condition. One of skill in the art recognizes that an amount or time period may be considered therapeutically effective even if the wound or condition is not totally eradicated but improved partially. The composition can be changed or re-applied daily, or multiple times per day. Likewise, the composition can be applied every other day, every three days, etc. Those skilled in the art will appreciate that treatment protocols can vary depending upon the wound, healing status, and preference of the practitioner.

For example, occurrences of equine dermatitis in all manner discussed previously, and any type of inflammation of the skin, with the causes of skin inflammation, including external irritants, burns, allergens, trauma, and infection (bacterial, viral, parasitic, or fungal), abnormal itching, called pruritus, occurs in many skin diseases, and creates an extremely complicated approach to treatment. As the inflammation progresses, crusting and scaling develop and have been effectively treated with the inventive composition by cleaning the affected area with water or a saline solution followed by application of the composition to the affected area. The area may be rinsed conservatively after each 24 hour period and the composition reapplied until signs of infection and inflammation resolve.

Advantageously, the compositions, methods, and treatment protocols can consist of use of only the disclosed composition (invention) in the treatment of the wound or skin condition. In other words, no other adjunctive therapy is required to initiate or promote healing. As such, in some embodiments, the only therapeutic or "active" agent used in treating the wound or skin condition is preferably the unique composition of this invention. No other antibacterial compositions, ointments, hydrogels, therapeutic dressings, and the like are needed, and can preferably be avoided under typical circumstances. Notwithstanding the foregoing, it will be understood that the methods and treatment protocols would still encompass the use of passive wound care items, such as non-occlusive bandages and gauze, etc. that can be used to cover the treated wound or inflammatory condition once the modified collagen gel has been applied or administered.

Infectious conditions treatable with the inventive compound include, but are not limited to, fungal dermatitis models (also known as greasy heel, cracked heels, mud fever, dew poisoning or equine pastern dermatitis), as well as superficial skin disorders and infection of direct wounds. Physical injuries, such as degloving injuries in equines, bite wounds in canines, or other superficial or various depth injuries may be treated with the composition. Immunological conditions, such as allergies, other superficial or various depth injuries may be treated with the composition.

In various aspects, the infection or disease to be treated is caused by an infectious agent selected from the group consisting of bacteria, virus, fungus, parasite, and protozoan.

In various aspects, the bacteria is selected from the group consisting of *Porphyromonas gulae, Brevibacterium* species, *Weeksella zoohelcum, Pediococcus damnosus, Stomatococcus mucilaginosus, Pasteurella canis, Pasteurella multocida* sub sp. *multocida, Pasteurella stomatis, Pasteurella* multocida subsp. *septica*, *Pasteurella dagmatis*, *Pasteurella multocida* subsp. *Gallicida*, *Streptococcus mitis*, *Streptococcus mutans*, *Streptococcus pyogenes*, *Streptococcus sanguis*, *Streptococcus sanguis* biotype I, *Streptococcus sanguis* biotype II, *Streptococcus* group F, *Streptococcus intermedius*, *Streptococcus constellatus*, *Streptococcus equinus*, *Streptococcus agalactiae*, beta-hemolytic *Streptococcus* group G, *Streptococcus dysgalactiae*, *Staphylococcus aureus*, Methicillin-resistant *S. aureus* (MRSA), *Staphylococcus epidermidis*, *Staphylococcus warneri*, *Staphylococcus hominis*, *Staphylococcus auricularis*, *Staphylococcus cohnii*, *Staphylococcus xylosus*, *Staphylococcus intermedius*, *Staphylococcus pseudintermedius*, *Staphylococcus delphini*, *Neisseria weaveri*, *Neisseria zoodegmatis*, *Neisseria animaloris*, *Neisseria subflava*, *Corynebacterium* group G, *Corynebacterium aquaticum*, *Corynebacterium jeikeium*, *Corynebacterium afermentans*, *Corynebacterium* group E, *Corynebacterium pseudodiphtheriticum*, *Corynebacterium freiburgense*, *Enterococcus faecalis*, *Gemella morbillorum*, *Escherichia coli*, *Bacillus firmus*, *Actinomyces viscosus*, *Proteus mirabilis*, *Stenotrophomonas maltophilia*, *Bergeyella zoohelcum*, *Moraxella catarrhalis*, *Enterococcus avium*, *Enterococcus malodoratus*, *Bacillus circulans*, *Bacillus subtilis*, *Pseudomonas aeruginosa*, *Pseudomonas vesicularis*, *Pseudomonas diminuta*, *Actinomyces neuii* subsp. *anitratus*, *Klebsiella oxytoca*, *Klebsiella pneumoniae*, *Lactobacillus lactis*, *Citrobacter amalonaticus*, *Citrobacter koseri*, *Flavobacterium* group IIa, *Flavobacterium brevis*, *Micrococcus lylae*, *Capnocytophaga ochracea*, *Eikenella corrodens*, *Flavimonas oryzihabitans*, *Dermabacter hominis*, *Oerskovia* species, *Pediococcus damnosus*, and *Stomatococcus mucilaginosus*, *Capnocytophaga canimorsus*, *Capnocytophaga cynodegmi*, *Capnocytophaga ochracea*, *Capnocytophaga gingivalis*, *Capnocytophaga sputigena*, *Fusobacterium nucleatum*, *Bacteroides tectus*, *Propionibacterium acnes*, *Propionibacterium avidum*, *Propionibacterium lymphophilum*, *Propionibacterium acidipropionici*, *Propionibacterium freudenreichii*, *Prevotella intermedia*, *Peptostreptococcus anaerobius*, *Porphyromonas macacae*, *Porphyromonas cansulci*, *Bacteroides tectus*, *Prevotella bivia*, *Prevotella heparinolytica*, *Bacteroides uniformis*, *Tannerella forsythia*, *Campylobacter gracilis*, *Campylobacter ureolyticus*, *Porphyromonas canoris*, *Porphyromonas cangingivalis*, *Prevotella zoogleoformans*, *Fusobacterium russii*, *Fusobacterium gonidiaformans*, *Fusobacterium alocis*, *Bacteroides tectus* group E, *Bacteroides fragilis*, *Bacteroides ovatus*, *Porphyromonas circumdentaria*, *Porphyromonas levii*-like, *Prevotella melaninogenica*, *Prevotella denticola*, *Peptostreptococcus asaccharolyticus*, *Lactobacillus jensenii*, *Veillonella parvula*, *Porphyromonas salivosa*, *Prevotella bivia*, *Fusobacterium canifelinum*, *Staphylococcus sciuri* subsp. *lentus*, *Staphylococcus capitis*, *Staphylococcus haemolyticus*, *Staphylococcus hyicus*, *Staphylococcus saprophyticus*, and *Staphylococcus simulans*, *Neisseria cinerea*-*Neisseria flavescens* (2%), and *Neisseria* mucosa, *Neisseria canis*, *Corynebacterium minutissimum*, *Corynebacterium* group B, *Corynebacterium* group F-1, *Corynebacterium kutscheri*, *Corynebacterium propinquum*, *Corynebacterium striatum*, *Enterococcus durans*, *Bacillus firmus*, *Haemophilus felis*, *Corynebacterium diphtherias*, *Bartonella henselae*, *Bartonella clarridgeiae*, *Enterobacter cloacae*, *Erysipelothrix rhusiopathiae*, *Riemerella anatipestifer*, *Rothia dentocariosa*, *Aeromonas hydrophila*, *Pantoea agglomerans*, *Filifactor villosus*, *Clostridium sordellii*, *Actinobacillus suis*, *Actinobacillus lignieresii*, *Actinobacillus equuli*, and *Pasteurella pneumotropica*, and species of the genera *Rhodococcus* species, *Acinetobacter* species, *Alcaligenes* species.

In various aspects, the virus is selected from the group consisting of papilloma virus.

In various aspects, the fungus is selected from the group consisting of *Blastomyces dermatitidis*, *Microsporum Gypseum*, *Cryptococcus gattii*, *Coccidioides immitis*, *Cryptococcus neoformans*, *Histoplasma farciminosum*, *Pythium insidiosum*, *Rhinosporidium seeberi*, *Sporothrix schenckii*, *Conidiobolus coronatus*, *Conidiobolus lamprauges*, *Trichophyton equinum* and *Trichophyton mentagrophytes*, *Wangiella dermatitidis*, and species of the genera *Exophiala*, *Phialophora*, *Bipolaris*, *Exserohilum*, *Cladophialophora*, *Phaeoannellomyces*, *Aureobasidium*, *Cladosporium*, *Curvularia*, and *Alternaria*.

In various aspects, the parasite is selected from the group consisting of *Habronema muscae*, *Habronema majus* (*H. microstoma*), *Draschia megastoma*, *Onchocerca cervicalis*, *Parafilaria multipapillosa*, and *Pelodera strongyloides*.

In various aspects, the disease or condition is selected from the group consisting of Pastern dermatitis, Malanders, Sallenders, Feather Mites Dermanyssusgallinae, Dermatophytosis, Methicillin-resistant *S. aureus* (MRSA), allergies, allergic contact dermatitis, hives, insect bite hypersensitivity, *pemphigus foliaceus*, greasy heels or scratches, injection site reactions, rain rot, rain rot, *Dermatophilus congolensis*, pruritus, Aural plaques.

In various aspects, the composition is administered by a route of a topical application.

In various aspects, the composition is administered at a dose sufficient to completely cover the extent of the treatment site.

In various aspects, the treated animals are equines, including horses, donkeys, and mules.

In various aspects, the treated animals are canines.

In various aspects, the treated animals are felines.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

General composition: 62% to about 75% water, 0.1% to about 0.2% nitrofuracin, 0.1% to about 0.03% benzalkonium chloride, 25% to about 30% emollients (per list).

In one aspect, a composition was prepared by mixing a 350 mL solution of 0.2% w/w nitrofurazone dissolved in polyethylene glycol with a 90 mL solution of 0.15% w/w benzalkonium chloride and 0.045% w/w allantoin in water, along with a red dye. The resulting composition had a gel-like consistency.

Example 2

A orphaned weanling feral foal of approximately four months of age, obtained from an equine rescue organization. Upon separation from her mother, the foal was observed to have a degloving injury on the right hip in the region of the biceps and femoris. The wound at time of rescue was approximately six weeks old and due to the Feral nature of the animal, had not received any treatment and the wound had become infected and unhealed. The injury site measured approximately 20 square inches (FIG. 1A).

Figure 1B:
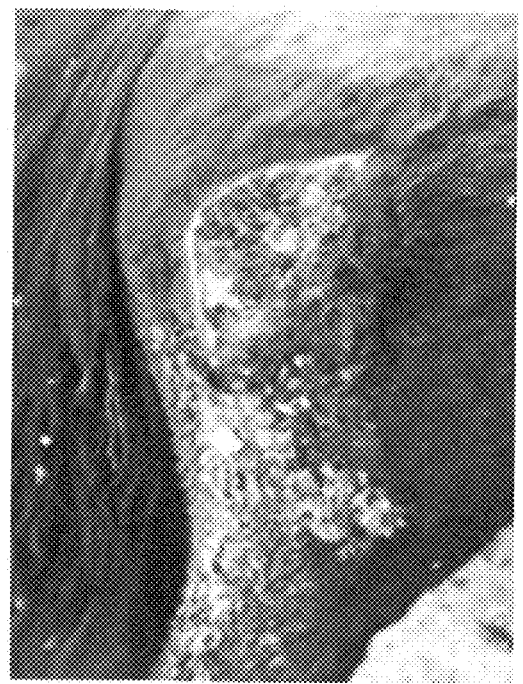

The filly was brought to a barn for examination for the extent of the injury. This is noted as Day 0 (prior to any application of invention). Excessive serous exudate had accumulated from the draining abscess on the wound and left a heavy-crusted suppuration on the hind leg (See FIG. FIG. 1B). A black spot appeared to be a scab over a portion of the degloved area as well as a yellow pocket that served as the source of the pus. The wound had drained a great deal of serous exudate and has a black area of severe infection that appears to be a deep pocket which has exuded pus for weeks as evidenced by the crusty purulent wound drainage which is a reflection of infection. All margins of the wound and though the photo does not exhibit the color accurately, pale flesh reflects the lack of circulation, oxygenation and no opportunity for epithelization.

Figure 2:
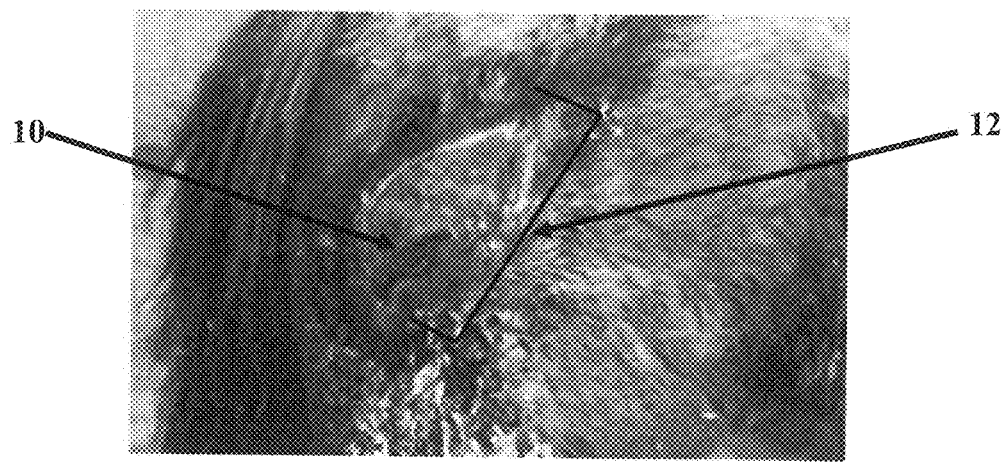
FIG. 2 is photograph of the degloving injury after cleaning and irrigation.

The area was cleared of the encrustation using a mild soap in saline which exposed the wound for closer examination. FIG. 2 illustrates the cleaned area with black scab (10) and elongated pustule (12).

Figure 3:
FIG. 3 is a photograph of the degloving injury with the inventive composition applied to the wound area.

Because this region does not easily permit wrapping, the product was applied as a primary dressing without the addition of a secondary or occlusive dressing (FIG. 3). 24 hours after the first application of product (Day 1), the wound was cleaned with saline solution and examined. The area of the wound where the purulent drainage originated is now toward the surface of the dermis. The amount of drainage is decreased. The margins are exhibiting brightening from oxygenation which will enable the keratinocytes to work their way from the edges toward the center of the wound and thereby form a new epidermal layer for the first time.

Figure 4:
FIG. 4 is a photograph of the progression of wound healing 24 hours after application of the composition.

In the first 24 hour time frame, the black scab over the source of exudation is about to fall off (FIG. 4) Under the scab is an abscess with the excess of dead white blood cells. The filly is in less pain and has allowed picking off of a loose part of scab. The inventive product was reapplied as above and left for another 24 hour period.

Figure 5:
FIG. 5 is a photograph of the wound area after 48 hours.

On Day 2, the area was again examined and photographed (FIG. 5) before and after washing the area with saline, the scab and pustule now reduced in size and yellow are both improved with less oozing of puss and the wound is taking on a drier, less inflamed appearance and no indication of ongoing infection. The product was again applied to the area and left.

Figure 6:
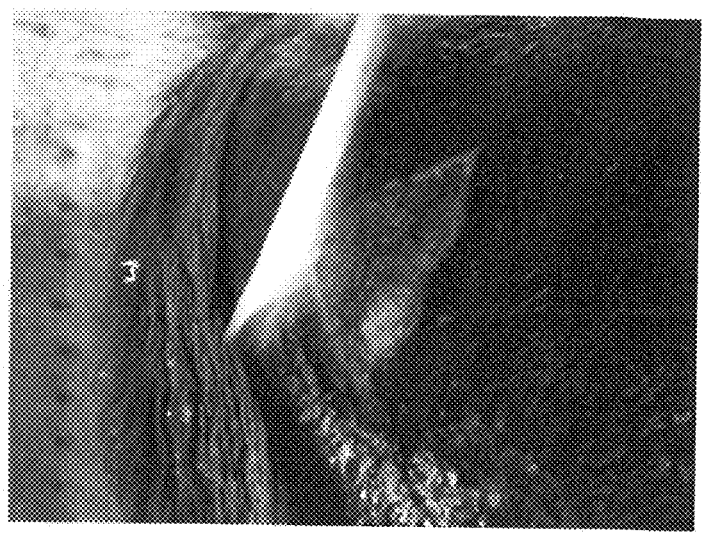
FIG. 6 is a photograph of the wound area after 72 hours.

On Day 3, the process was repeated. At this time the yellow pustule is on the surface and is no longer producing exudate. (FIG. 6). Epithelialization around the abscess, vascularity and oxygenation are starting to be apparent. The blood flow is improving to damaged tissues as evidence by the bright red areas of the wound. Oxygen and nutrients required to support the growth and function of reparative cells will help the wound improve.

Figure 7:
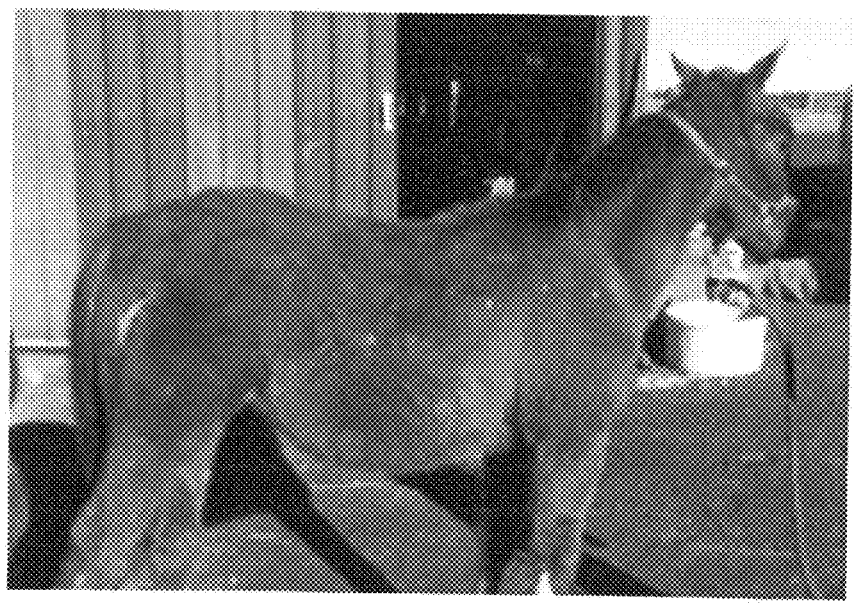
FIG. 7 is a photograph of the foal after wound healing.

Simple saline cleansing and re-application of product was repeated daily. The size and appearance of the wound continued to improve as new skin closed above the wound site. Throughout the process, the wound remained clear of any new signs of infection or inflammation. These results were especially unexpected as the wound was never able to be covered with a secondary or occlusive dressing as standard protocols would prescribe if wound was in a more advantageous location. The injury had completely healed leaving only a hairline crescent-shaped scar at the site of the injury, as shown in (FIG. 7).

Example 3

Figure 8:
FIG. 8 shows photographs of a horse pastern presenting with inflammation and dermatitis (A) and a close up view (B) of the inflamed tissue.
Figure 8:
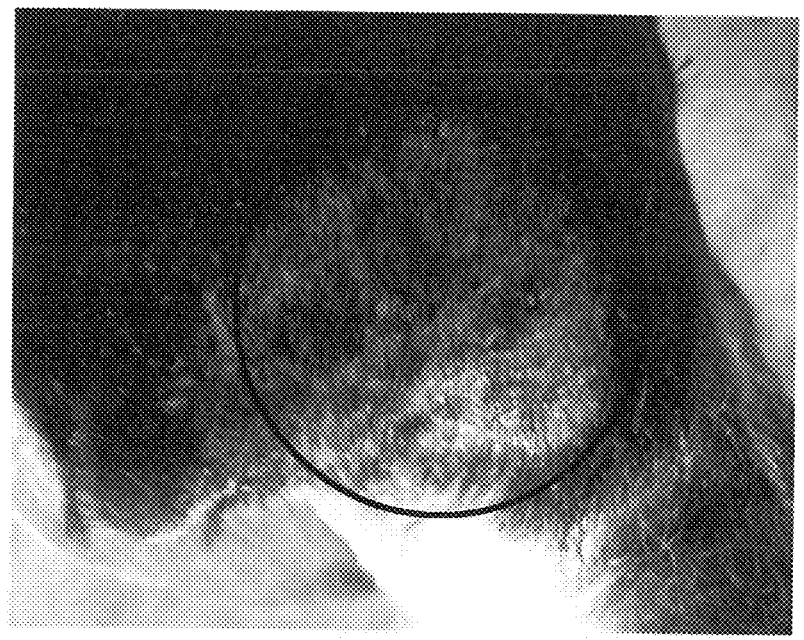

A 20 year old Quarter Horse mare used in cutting, reining and cowhorse performance events presented with signs of an abrasion wound inflammation and a type of fungal dermatitis was treated using the present invention. The mare was brought in from pasture on Day 0 exhibiting tenderness and inflammation on the right hind pastern. Because part of this pastern is white, and unpigmented skin is more susceptible to chaffing and abrasion, it was not surprising to observe some dermatitis, commonly called "Scratches" in this area. The inflammation had moved into the black area on the actual fetlock joint. FIGS. 8(A) and (B) illustrate the extent of the inflammation on Day 0. It is important that the increasing infection and inflammation are contained and decreased. As in any Pastern Dermatitis, the skin around the pastern and heel bulbs have become sensitive, exhibit the pale skin of scratches that indicates a lack of vascularity and the skin has hard crusty scabs. FIG. 8(A) exhibits the dryness of the fungal dermatitis on the back of the pastern and the heel bulbs.

The inventive product was applied to the areas described using a cotton gauze followed by a wrap of Cast Padding, and finally covered with co-heist bandage material and left to rest 24 hrs. No antibacterial soaps or other substances were applied to the injured area other than the inventive product.

24 hours later (Day 1), wrappings were removed and the injured area was photographed (FIG. 9(A)) and examined for the appearance of fungal dermatitis, inflammation & irritation. The area of the initial inflammation was dramatically improved. The bright pink skin has now become a sign of improvement as the pink usually appears in the first 24 hours. The inflammation on the area of the fetlock has lost it's inflamed, irritated appearance. Product was reapplied to area and wrapped in same manner as described above.

Figure 9:
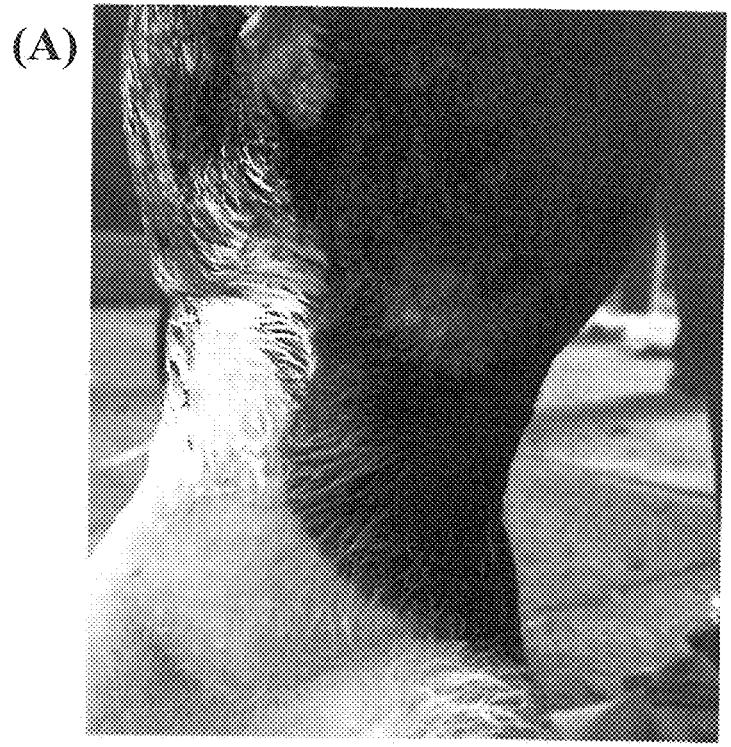
FIG. 9 is a photograph of (A) the inflamed tissue 24 hours after application of the inventive composition, and (B) the same tissue 48 hours after application of the inventive composition.
Figure 9:
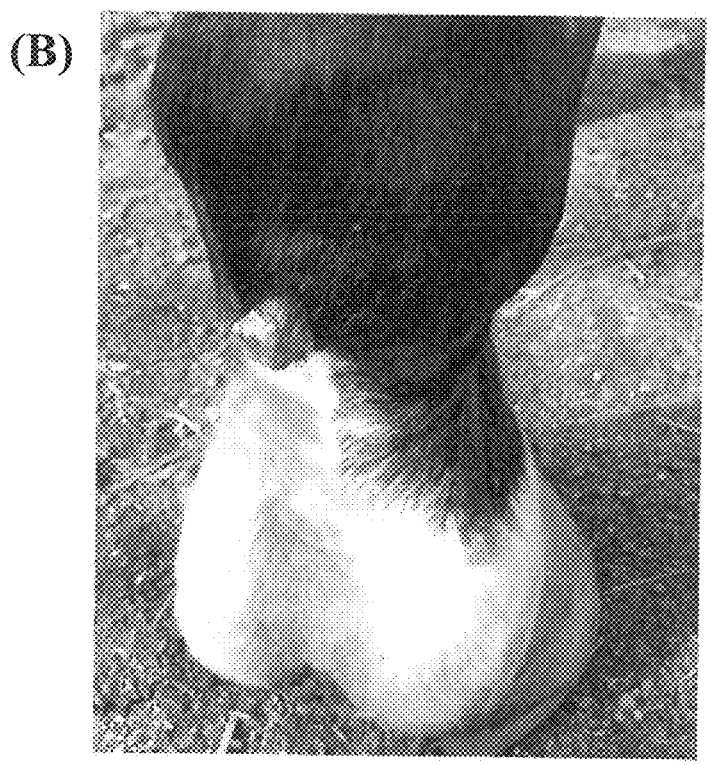

At 48 hours (Day 2), the foot was unwrapped, photographed (FIG. 9(B)) and examined as above. While there is a small area of red showing on the original location of the abrasion, the inflammation is greatly reduced.

The Scratches (fungal dermatitis) are completely removed from the area from heels to fetlock. The bright pink exhibited in the first 24 hours of fresh oxygenation has subsided due to the resolution of the dermatitis.

With regard to the abrasion wound, the invention has demonstrated an ability to quickly reduce the inflammation and decrease the proliferation of the dermatitis to the surrounding tissue. It accelerates the resolution of the wound and the regeneration of healthy functional derma.

Example 4

Figure 10:
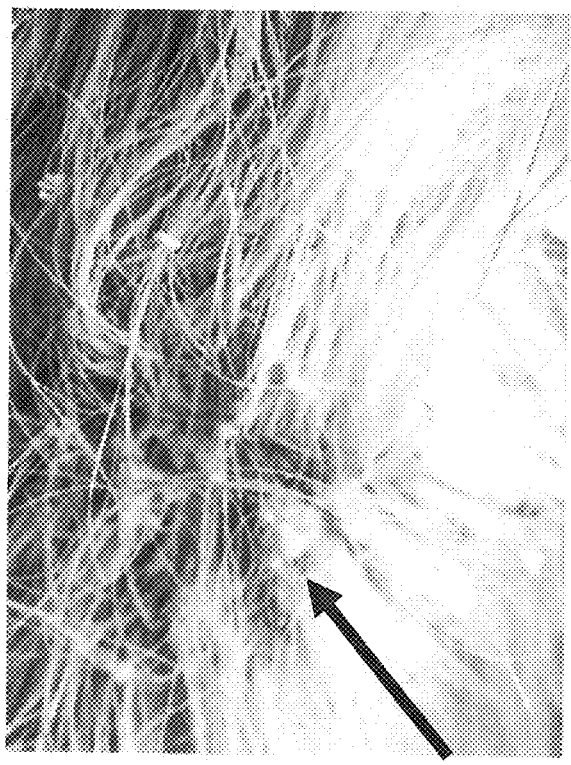
FIG. 10 is a photograph of "feathers" of a Gypsy draft horse chronically infected with fungal dermatitis (arrow pointing to nodules).

A Draft breed horse mare with unusual and long term fungal dermatitis in the area of its 'feathers' was purchased with the condition preexisting on all four legs (FIG. 10). At the time of purchase, it was reported that this Gypsy, a breed of draft horses, had suffered from dermatitis for at least four years.

This particular animal had extensive feathers on all four legs, which, upon close inspection, the owner pointed out signs of fungal dermatitis which she called scratches. Other-breeders of these animals call the condition 'Malanders.' These signs included sores, scabs, and tenderness on all four legs from the knee down the pastern in front and below the hock to pastern in the hind. This animal was extremely sensitive in the affected area and was unwilling to allow veterinarians or handlers to comb through the hair of the feathers or remove the scabs without sedation followed by aggressive scraping and cutting. While the owner called the presentation "Scratches", a local veterinarian familiar with the dermatitis, diagnosed the causation as "Feather Mites" aka Chorioptic mange mites on all four legs.

What makes this case interesting is the size of the grape- and pea-sized round nodules that are attached to the leg and leg hairs (feathers) and protrude from a small attachment area of the skin on the leg. (FIG. 10) The aggregate of the nodules and the smaller grain sized nodules is large. The small nodules appear to be growing into large papules. The presenting nodules are rubbery, white and there is no real possibility of surgical removal without significant discomfort. The affected area is from the back of the knee to the heel bulb on each leg.

FIG. 10 illustrates the nodules, which appear in texture and firmness similar to small, white round "buds," as they appeared on day 0. Although these apparent nodules were widespread, the largest nodules were found on the backs of the legs.

Figure 11:
FIG. 11 is a photograph of the application of the inventive composition to the feathers.

To apply the invention to the areas afflicted, it was necessary to manually pull strands of the feathers away from the horse and saturate them with the ointment, as shown in FIG. 11. The owner did not want the feathers clipped off and on this first day of examination, it was soon apparent that it would not have been possible to clip the hair due to the abundance of nodules and efflux. It is illustrated in the photo, the process using the invention (with green due to dye added to help visualize the treatment). Once the area was sufficiently covered, the legs were wrapped in soft cotton gauze padding and cohesive bandage material and left to rest 24 hrs. No antibacterial soaps or other substances were applied to the injured area other than the inventive product.

Figure 12:
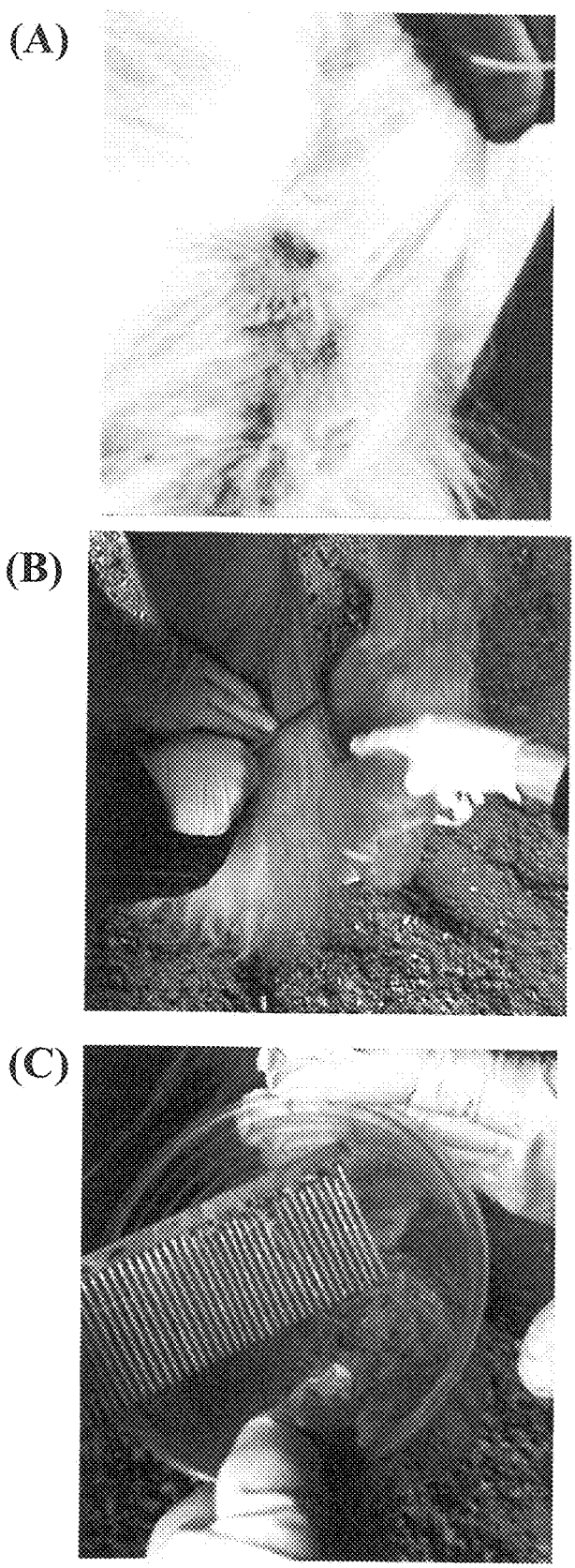
FIG. 12 shows photographs of (A) the horse infected area 24 hours after application of the inventive composition, followed by (B) removal of scabs, and (C) combing of the feathers.

On day 1 (24 hours after application), the wrapping was removed and the area was inspected and photographed. At this time the hair was free of scabs, nodules, or heavy encrustation found the previous day (FIG. 12(A)). All of the large round "buds" were also gone and fresh blood was apparent on the skin in the areas where they had been located. Further, the hair was easily combed without apparent pain to the animal allowing for removal of any remaining scabs that had been loosened. (See FIGS. 12(B) and (C)).

Figure 13:
FIG. 13 is a photograph of the previously-infected horse feathers 48 hours after initial application of the inventive composition and re-application at 24-hours.

Treatment and wrapping were repeated as described above and left for an additional 24 hrs. On day 2 (FIG. 13), the skin remained pink and no new encrustation was observed. Treatment and wrapping were again repeated. On day 3, the horse was seen by a veterinarian who confirmed that the condition was successfully resolved.

Example 5

Figure 14:
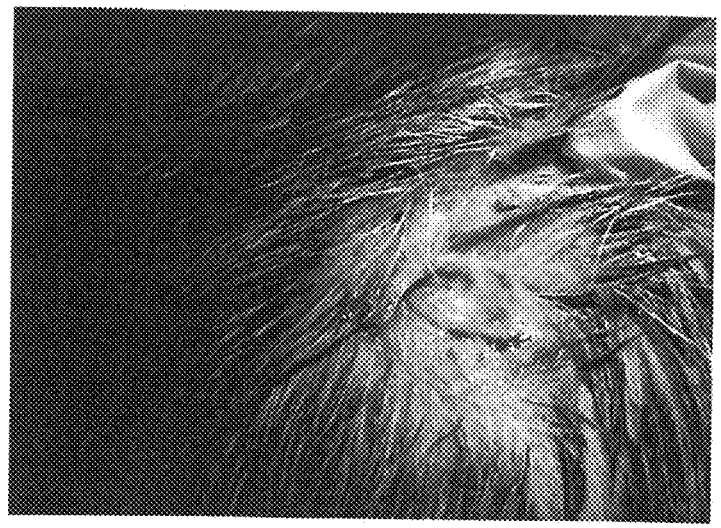
FIG. 14 is a photograph of a bite wound on a canine treated in Example 5.
Figure 15:
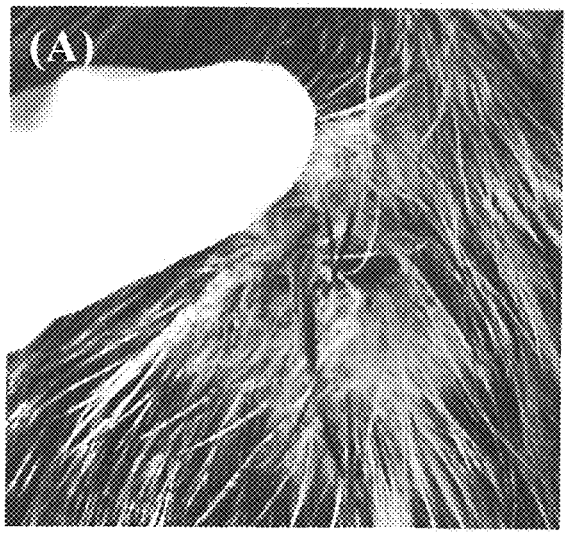
FIG. 15 shows photographs of wound progression in Example 5, on (A) day 1, (B) day 2, (C) day 3, and (D) day 4 after application of the inventive composition to the wound area.
Figure 15:
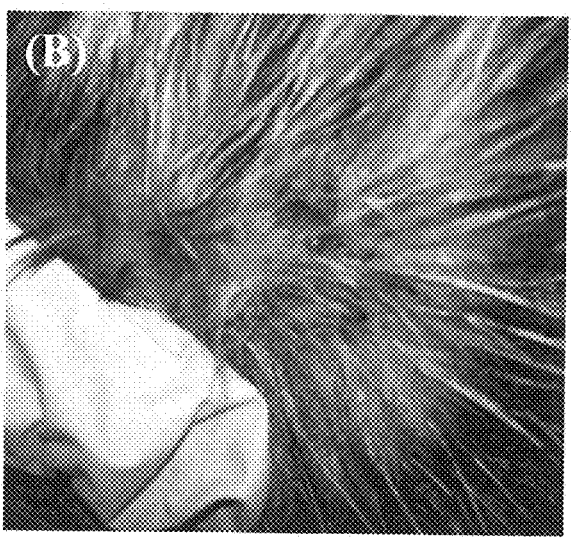
Figure 15:
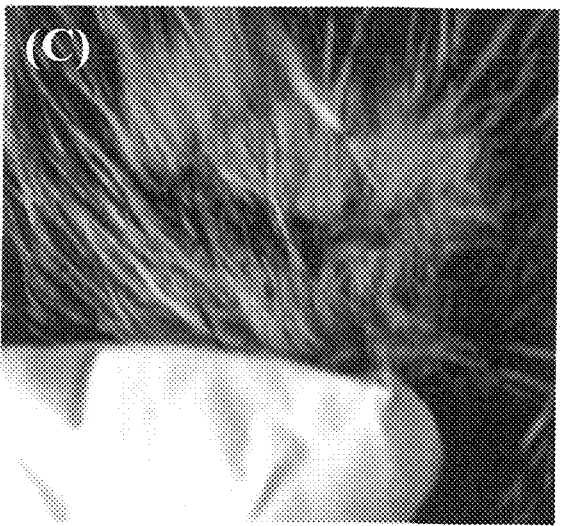
Figure 15:
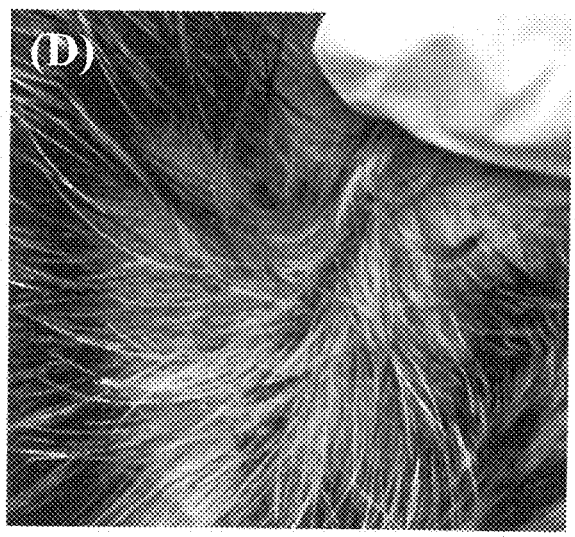

An example of treating a bite wound on a canine is presented herein. Following the introduction of a one year old male heeler cross with a new family of dogs, the healer was bitten on the shoulder, resulting in a significant tear in the skin (FIG. 14). The location of the injury precluded an effective wrap to prevent infection and further injury. The wound was flushed using a saline solution and the inventive composition was applied liberally over the area. No additional product or further wrapping was applied. As, described above, the area was flushed with saline daily and fresh application of invention was applied. FIG. 15 illustrates the progress over the following days, where the wound area is was photographed on day 1 (FIG. 15(A)), day 2 (FIG. 15(B)), day 3 (FIG. 15(C)), and day 4 (FIG. 15(D)), respectively. By day 2, the wounded area did not appear to be swollen or inflamed in any way. On day 3, the open areas had scabbed over and on day 4 the wound was nearly resolved.

Example 6

Figure 16:
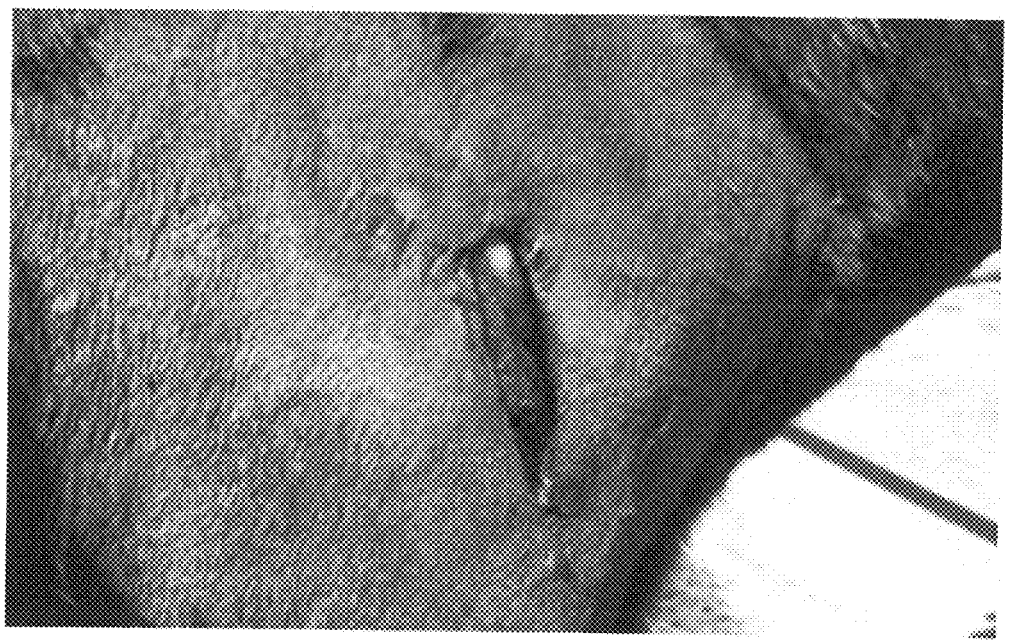
FIG. 16 shows (A) a photograph of a deep wound on a horse, right side of neck, and (B) a close-up image of the same wound.
Figure 16:
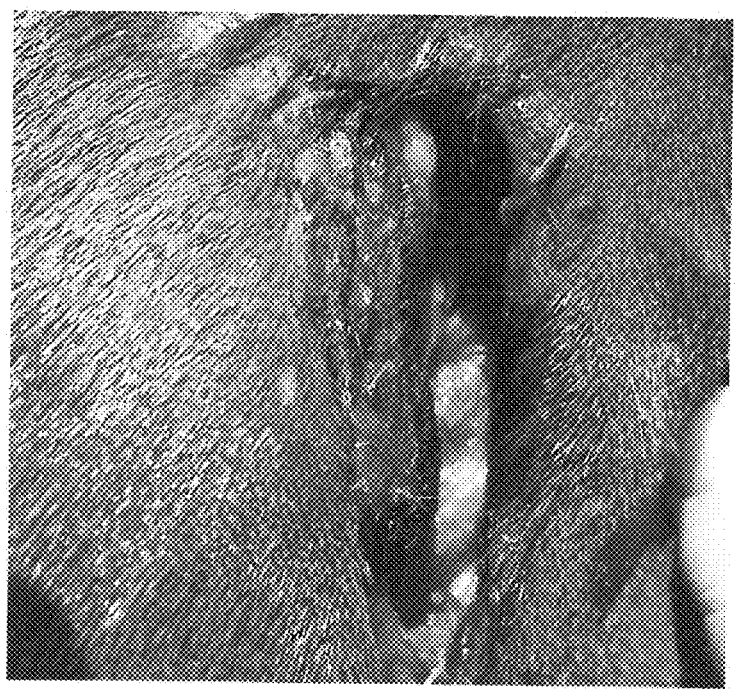
Figure 17:
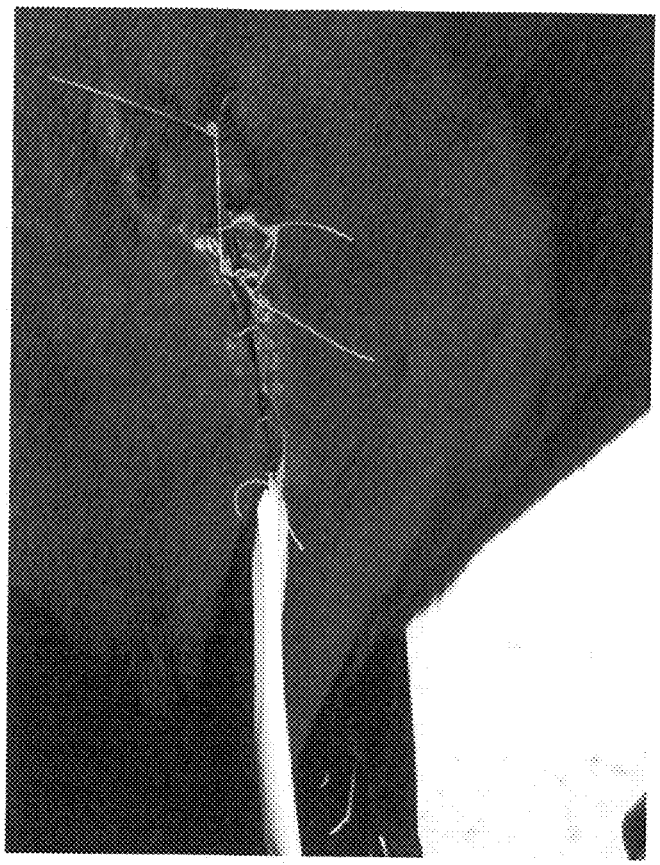
FIG. 17 is a photograph of the wound stitched with a drain tube.

A 20-year old performance mare presented with a large, deep gash across the right side of the neck. (See FIGS. 16(A) and (B)). The wound was very deep going through several layers of the neck. It had pierced the epidermis, dermis, the sub cutaneous layer and, additionally, the wound was not fresh and apparently happened several hours before in the night. This non-fresh wound decreases the chance for perfect healing. The wound was fated to have a high possibility of scarring, hair color change, infection, and a long period of time for healing. A veterinarian was called and stitching which was done 24 hours after discovery of the wound, the drain (FIG. 17) which was inserted into the stitches was of no use as it had accidentally been closed under the stitches, thus not allowing drainage through the tube. The wound remained largely open and was expanding rather than healing causing the owner to become concerned. The wound was splitting open and the margins were torn from the stitches. The drainage of dead white cells, and other serous exudate from the interior of the wound were at an extreme level. All remaining parts of the stitching and the drain were carefully removed from the wound area.

The invention was inserted through the openings in the wound line by a syringe, additionally the unwrappable wound was covered with the invention which continued three times a day for four days. At that point, much of the fill-in of the area had healthy tissue and invention application was moved to 2× per day.

Figure 18:
FIG. 18 is a photograph of the wound area after application of the inventive composition 2 times per day to the wound site over a period of weeks.

Within three days the wound stopped draining the exudate and color started to appear at the margins, exhibiting restoration of blood flow to damaged tissues and providing oxygen to the area. The possibility of oxygen means circulation and thus epithelization. (See FIG. 18).

Example 7

A Warmblood Dressage horse presented with Scratches on both hind pasterns (FIGS. 19(A) and (B)). This was according to the owner a chronic, 4-year old condition. This equine did present a case of fungal dermatitis, and after clearing up the Scratches, it became apparent that the horse also had very old wounds or damage to the pasterns that were mistaken for "Scratches".

The horse was extremely sensitive and had an issue with touching or examining the affected area. The dermatitis has been on the horse for a minimum of four years.

A new batch of the inventive composition was applied to the legs. The treatment protocol involved daily application with wrapping of the pasterns and fetlock to coronet band. After 24 hours, immediate improvement was visible (FIGS.

19(C) and (D)). At this juncture, the majority of the hard scabby surface has been cleared of the detris.

The invention has the advantage of the bright skin color exhibiting vascularity and oxygenation to the tissue that had been inhibited from cell rejuvenation in the shortest period of time. The bright skin is a trademark of the invention and is a remarkable key to the removal of the dermatitis. The equine obviously suffered a deep gash to the right hind heel bulb. The gash did not completely heal and left a surface for keloid material to develop to protect the wound damage when it is not fully healed.

The left hind shows where fissures had opened in the skin and thick, fibrous, granular scar tissue had begun to form. As oxygenation constantly improves, the fissures will lose their heavy keloid crust, and then the original wound can start to complete the healing.

Each day the pastern will receive an application of the invention and will be wrapped with bandage, cast padding and cohesive wrap.

After 48 hours, the 4-year old wounds that were covered with the Scratches are regaining cell rejuvenation and the tissue at the large cut will start to have epithelization to close the line of the cut including a large slice in the right heel bulb. On the left hind leg, the red blemish is an area that had been sored but was covered up with the scratches.

Three days from the first application of the invention on the horse with a four year old fungal dermatitis condition of the hind pasterns, the heels and pasterns of both legs have improved substantially. (FIGS. 20(A) and (B)). Additionally, the right hind with the severe wound to the right hind heel bulb is losing the heavy keloid scarring of the wound line. The invention is noted for this ability to decrease and remove keloids in more than one case.

Figure 20:
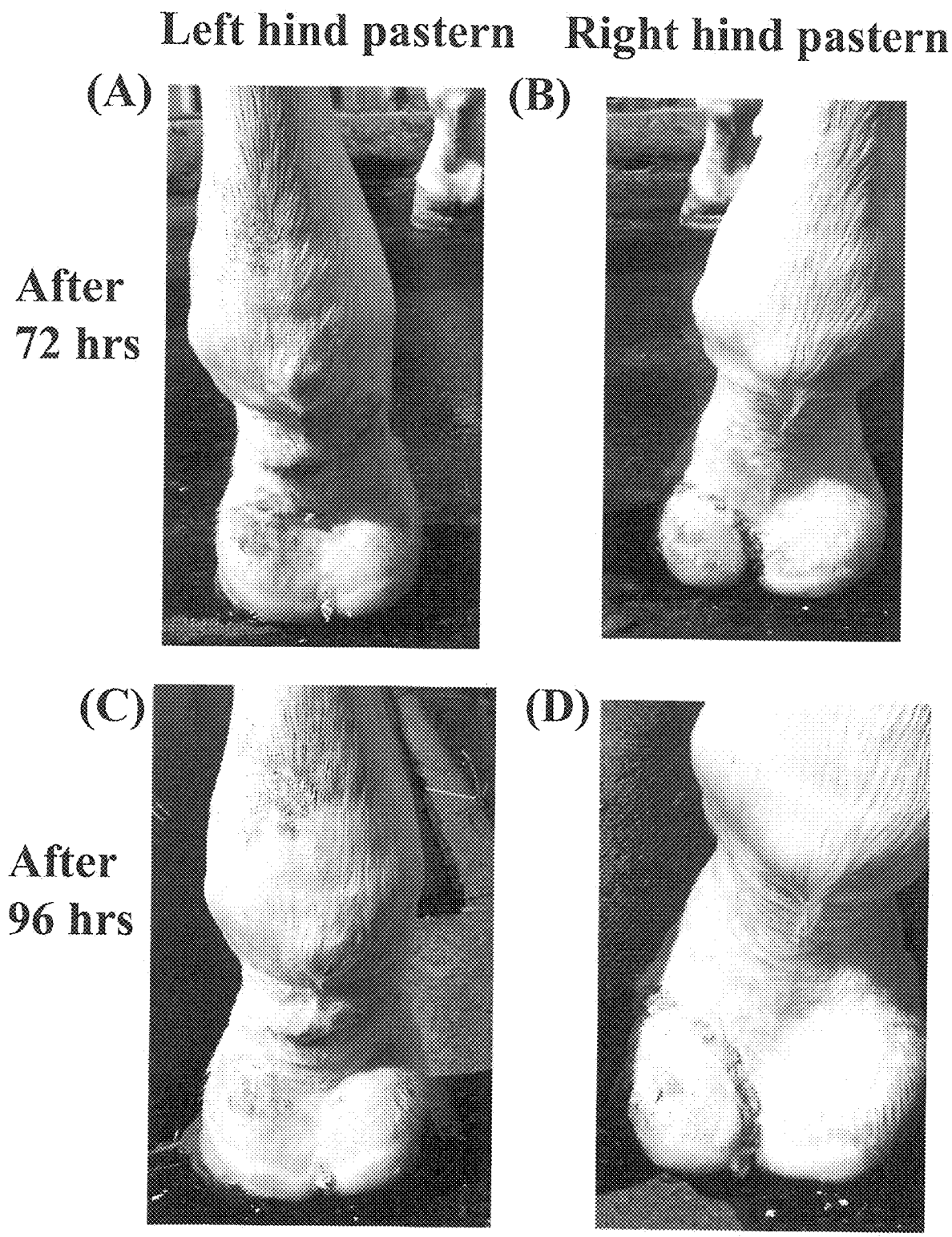
FIG. 20 shows photographs 72 hours after application of the composition to the (A) left and (B) right pasterns, followed by continuing improvement in the (C) left and (D) right pastern after 96 hours.

Four days from first application the progress noted continues to improve. As seen in FIGS. 20(C) and (D), both legs that for four years were suffering from fungal dermatitis and non-healing wounds are now, in four days, suddenly close to resolution.

Example 8

Figure 21:
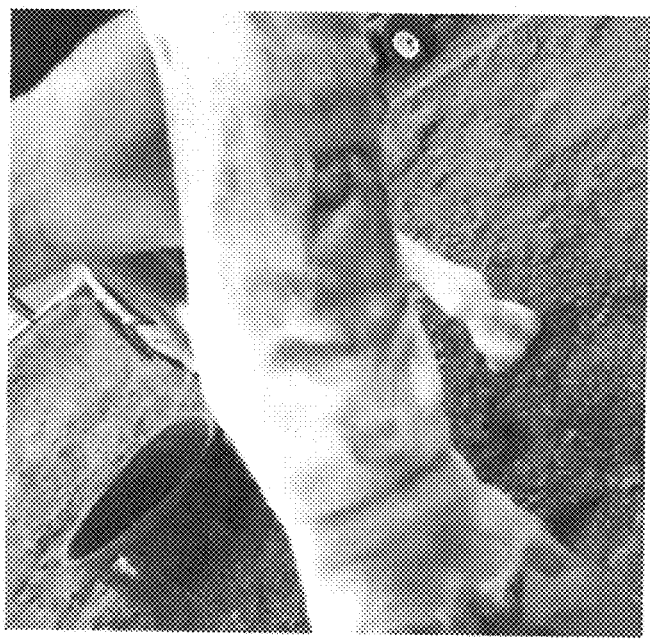
FIG. 21 is a photograph of a small wound on the back left leg of a horse.

A Thoroughbred Gelding presented a protruding wound that has changed the shape of the lower left hind leg above the fetlock joint. The protrusion of exuberant granulation tissue (EGT) and that EGT has mushroomed over the edges of the wound making healthy epithelialization impossible. The site was originally a small wound on the back of the left leg. (FIG. 21).

Figure 22:
FIG. 22 is a photograph of the wound after the granulated tissue was removed by a veterinarian.

The wound protruded so far from the skin layer that the veterinarian sliced off the extra granulation tissue and left a large open wound with a signification of excessive granulation still in the wound. This would mean to the owner that more mushrooming of the EGT would commence, further resisting the healing of this wound. (FIG. 22).

The Owner wished to have invention placed on the wound. Invention was applied and wrapping of the leg consisted of a bandage pad, cast padding and cohesive bandage material. Patient was checked every 48 hours. The first examination of the wound exhibited lessening of the excessive granulation tissue and margins of the wound became apparent.

Figure 23:
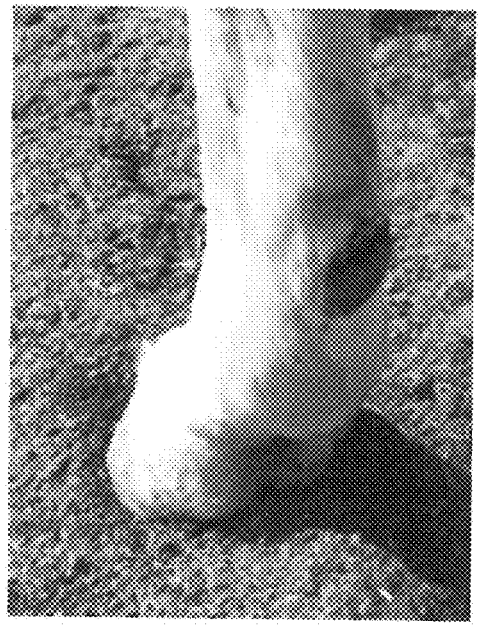
FIG. 23 is a photograph of the wound 48 hours after application of the composition.

In 48 hours, a posterior view of the wound clearly demonstrates that there is no additional growth of EGT present. The swelling which caused a deformation of the line of the leg has decreased and the margins of the wound are beginning to appear to have cell growth. (FIG. 23). The horse also demonstrated significantly less discomfort when the wound was treated. After cleaning with saline, the product was reapplied and the wrapping protocol was followed.

Figure 24:
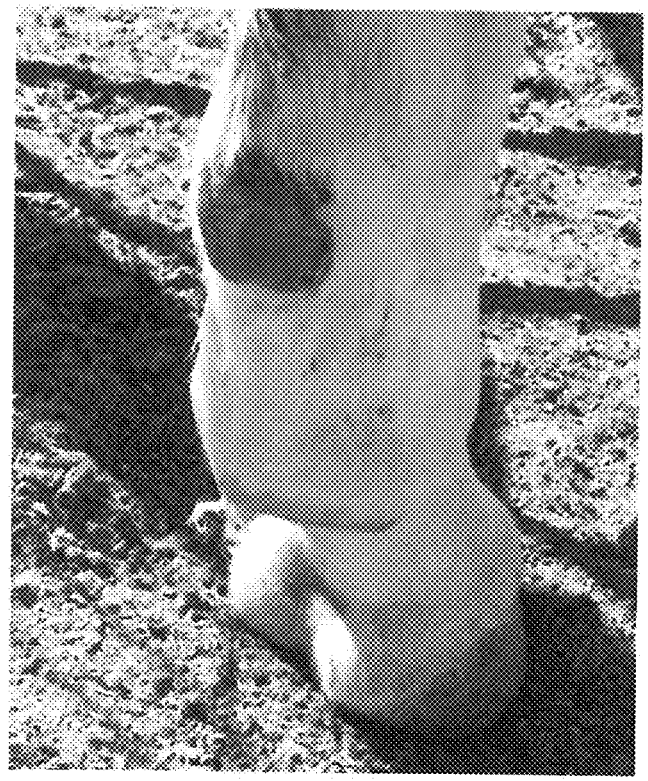
FIG. 24 is a photograph of the wound 96 hours after the initial application of the composition to the wound area.

In another 48 hours, the margins of the wound had deceased once again. Mushrooming of the edges had stopped. There is increased vascularity and oxygenation. (FIG. 24).

The wound continued to decrease in size throughout the duration of the test. Swelling is barely present and the protrusion of the wound from the leg was substantially reduced. There is no evidence of regrowth of exuberant granulation tissue, as the margins of the wound are light pink with oxygenation and fresh cellular growth.

Figure 25:
FIG. 25 is a photograph of the wound area 24 days after initial application of the composition, where the arrow indicates a small area with normal scabbing.

In 24 days, a normal scab (arrow) has formed on the wound. (FIG. 25). The horse had regained full function.

The invention claimed is:

1. A method of treating dermatitis skin conditions or wounds in an equine subject in need thereof, said method comprising:
applying a therapeutically effective amount of a composition to a site of said skin condition or wound of said subject to yield a treated site, said composition comprising: nitrofurazone, benzalkonium chloride, allantoin, water, polyethylene glycol, and an optional coloring agent, said composition comprising: from about 0.10% to about 0.20% of said nitrofurazone; from about 0.01 to about 0.05% of said benzalkonium chloride; and from about 0.005% to about 2% of said allantoin, wherein said composition has a gel-like consistency.

2. The method of claim 1 said composition consisting of nitrofurazone, benzalkonium chloride, allantoin, water, and polyethylene glycol.

3. The method of claim 1, further comprising:
covering said treated site with a dressing.

4. The method of claim 1, wherein said treated site is not covered with a dressing after said applying.

5. The method of claim 1, further comprising:
rinsing said treated site with a saline solution about 24 hours after said applying to yield a rinsed treatment site.

6. The method of claim 5, further comprising:
reapplying said composition to said rinsed treatment site.

7. The method of claim 1, wherein said skin condition is fungal dermatitis.

8. The method of claim 1, wherein said skin condition or wound is a chronic skin condition or wound.

9. The method of claim 1, wherein said site of said skin condition or wound of said subject is not contacted with an antibiotic cleanser or ointment before or after applying said composition to said site.

10. The method of claim 1, wherein said skin condition is Equine Pastern Dermatitis.

* * * * *